United States Patent
Muller et al.

(10) Patent No.: US 10,933,103 B2
(45) Date of Patent: Mar. 2, 2021

(54) **DERMATOLOGIC COMPOSITION CONTAINING *ESCHERICHIA COLI* AND *ENTEROCOCCUS FAECALIS***

(71) Applicant: SymbioGruppe GmbH & Co. KG, Herborn (DE)

(72) Inventors: Hans-Jorg Muller, Braunfels (DE); Thomas Michael Schmidts, Giessen (DE); Kurt Zimmermann, Herborn (DE); Volker Rusch, Herborn (DE)

(73) Assignee: SymbioGruppe GmbH & Co. KG, Herborn (DE)

( * ) Notice: Subject to any disclaimer, the term of this patent is extended or adjusted under 35 U.S.C. 154(b) by 135 days.

(21) Appl. No.: 16/202,409

(22) Filed: Nov. 28, 2018

(65) Prior Publication Data

US 2019/0160116 A1    May 30, 2019

(30) Foreign Application Priority Data

Nov. 29, 2017  (EP) .................................... 17204458

(51) Int. Cl.
| | |
|---|---|
| A61K 35/74 | (2015.01) |
| A61K 9/00 | (2006.01) |
| A61K 9/08 | (2006.01) |
| A61K 9/107 | (2006.01) |
| A61P 17/00 | (2006.01) |
| A61K 8/99 | (2017.01) |
| A61Q 19/00 | (2006.01) |
| A61K 8/06 | (2006.01) |
| A61K 9/06 | (2006.01) |
| A61K 35/00 | (2006.01) |

(52) U.S. Cl.
CPC ................ *A61K 35/74* (2013.01); *A61K 8/06* (2013.01); *A61K 8/99* (2013.01); *A61K 9/0014* (2013.01); *A61K 9/06* (2013.01); *A61K 9/08* (2013.01); *A61K 9/107* (2013.01); *A61K 35/00* (2013.01); *A61P 17/00* (2018.01); *A61Q 19/007* (2013.01)

(58) Field of Classification Search
CPC combination set(s) only.
See application file for complete search history.

(56) References Cited

FOREIGN PATENT DOCUMENTS

DE          69019956 T2    11/1995

OTHER PUBLICATIONS

Lau, S. et al., J. Allergy Clin Immunol. 2012, vol. 129, pp. 1040-1047.*
European Search Report dated Jun. 5, 2018 issued in corresponding EP17204458.8 application (10 pages).
English Abstract of WO 91/04742 A1 published Nov. 23, 1995 which corresponds to DE 69019956 T2.
S. Lau et al. "Oral Application of Bacterial Lysate in Infancy Decreases the Risk of Atopic Dermatitis in Children with 1 Atopic Parent in a Randomized, Placebo-Controlled Trial", Journal of Allergy and Clinical Immunology, vol. 129, No. 4 (Feb. 1, 2012) pp. 1040-1047.
Database Biosis [Online] Biosciences Information Service—XP-002780776 (Nov. 2013).
Database Biosis [Online] Biosciences Information Service—XP-002780777 (Jun. 2014).
J. Penders et al., "Establishment of the Intestinal Microbiota and its Role for Atopic Dermatitis in Early Childhood", Journal of Allergy and Clinical Immunology, vol. 132, No. 3 (Sep. 2013) pp. 601-607e8.

* cited by examiner

*Primary Examiner* — Heidi Reese
(74) *Attorney, Agent, or Firm* — Millen White Zelano and Branigan, PC; Csaba Henter

(57) ABSTRACT

Disclosed is a composition comprising an effective amount of a mixture of inactivated *Escherichia coli* and *Enterococcus faecalis* as well as pharmaceutically acceptable excipients and/or carriers for use in the treatment, supportive treatment or prevention of dermatologic conditions and diseases.

18 Claims, 2 Drawing Sheets

DERMATOLOGIC COMPOSITION CONTAINING ESCHERICHIA COLI AND ENTEROCOCCUS FAECALIS

PRIOR ART

The most important function of the skin is its barrier function, i.e. that of protecting the organism from drying out and external influences. The outer skin layer (epidermis) naturally plays a role in this function. It is the interface to the outside environment, and must constantly remain soft and supple. Skin hydration plays a highly significant role in this. Moisture in the skin acts in the epidermis as a softener in a system composed of lipid and protein structures that are replenished on an ongoing basis during the process of neoformation of skin.

There are various skin diseases that lead to dry skin, preventing the skin from providing this barrier function.

Pharmaceutical and cosmetic approaches for solving this problem are based on using substances that rehydrate the damaged tissue by means of moisture-providing compositions and/or preventing moisture loss by means of a protective layer.

The object of the invention is therefore to provide a novel composition used in the treatment, supportive treatment or prevention of dermatologic conditions and diseases.

SUMMARY

This object is achieved by the subject matter of the claims.

A pharmaceutical composition is therefore disclosed comprising an effective amount of a mixture of inactivated *Escherichia coli* and *Enterococcus faecalis* as well as pharmaceutically acceptable excipients and/or carriers for use in the treatment, supportive treatment or prevention of dermatologic conditions and diseases.

The composition may be in a topically applicable form.

*Escherichia coli* and *Enterococcus faecalis* can be present as a lysate.

The mixture of *Escherichia coli* and *Enterococcus faecalis* can be present in an amount of 1-95 wt %, 20-80 wt %, 40-60 wt % or 45-55 wt % of the total composition.

*Escherichia coli* and *Enterococcus faecalis* can be present in a ratio of between 0.5:1.5 and 1.5:0.5, 0.75:1.25 and 1.25:0.75, or 1.15:0.85 and 0.85:1.15 or 1.05:0.95 and 0.95:1.05 in the mixture.

*Escherichia coli* and *Enterococcus faecalis* can each be present in a cell count of $0.5 \times 10^7$ to $10 \times 10^7$, $1.0 \times 10^7$ to $7 \times 10^7$, or $1.5 \times 10^7$ to $4.5 \times 10^7$ per 100 g of the total mass.

The dermatologic disease or the dermatologic condition can be selected from dry skin, transepidermal water loss, inflammatory skin diseases, neurodermatitis or a combination thereof.

The composition can be in the form of an ointment, liquid, emulsion or solution.

Further disclosed is a cosmetic composition comprising an effective amount of a mixture of inactivated *Escherichia coli* and *Enterococcus faecalis*.

The cosmetic composition can be present in a topically applicable form.

*Enterococcus faecalis* can be present in the cosmetic composition in the form of a lysate.

The mixture of *Escherichia coli* and *Enterococcus faecalis* can be present in the cosmetic composition in an amount of 1-95 wt %, 20-80 wt %, 40-60 wt % or 45-55 wt % of the total composition.

*Escherichia coli* and *Enterococcus faecalis* can be present in the cosmetic composition in a ratio of 0.5:1.5 to 1.5:0.5, 0.75:1.25 to 1.25:0.75, or 1.15:0.85 to 0.85:1.15 or 1.05:0.95 to 0.95:1.05.

*Escherichia coli* and *Enterococcus faecalis* can be present in the cosmetic composition in respective cell counts of $0.5 \times 10^7$ to $10 \times 10^7$, $1.0 \times 10^7$ to $7 \times 10^7$ or $1.5 \times 10^7$ to $4.5 \times 10^7$ per 100 g of the total mass.

The indicated cosmetic application can be selected from dry skin or transepidermal water loss.

The cosmetic composition can be in the form of an ointment, liquid, emulsion or solution.

A method is further disclosed for producing a pharmaceutical composition or cosmetic composition, wherein an effective amount of inactivated *Escherichia coli* and *Enterococcus faecalis* and pharmaceutically or cosmetically acceptable excipients and/or carriers are mixed in order to obtain the above-mentioned dermatologically effective pharmaceutical or cosmetic composition.

DETAILED DESCRIPTION

Figure 1:
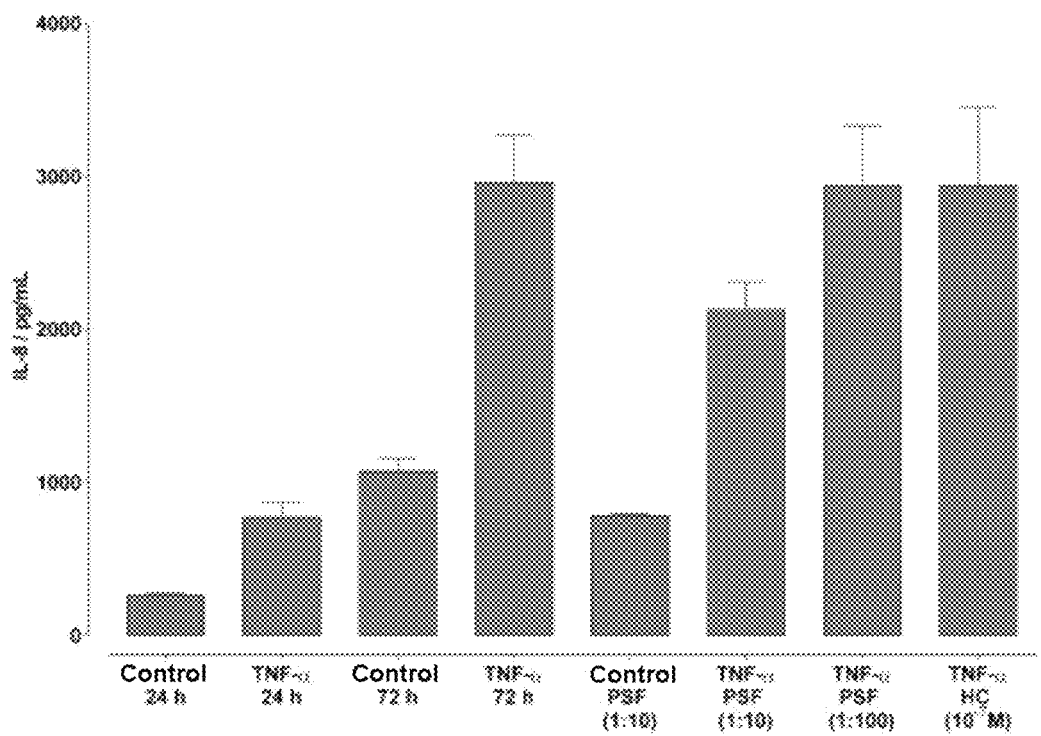
FIG. 1: Determination of IL-8 secretion in HaCaT cells after treatment with 10 ng/mL of TNFα (controls without TNFα) and incubation with the test substance (PSF) or hydrocortisone (HC) for 72 h (unless otherwise indicated), MV±SEM, n=3 (in triplicate respectively).
Figure 2:
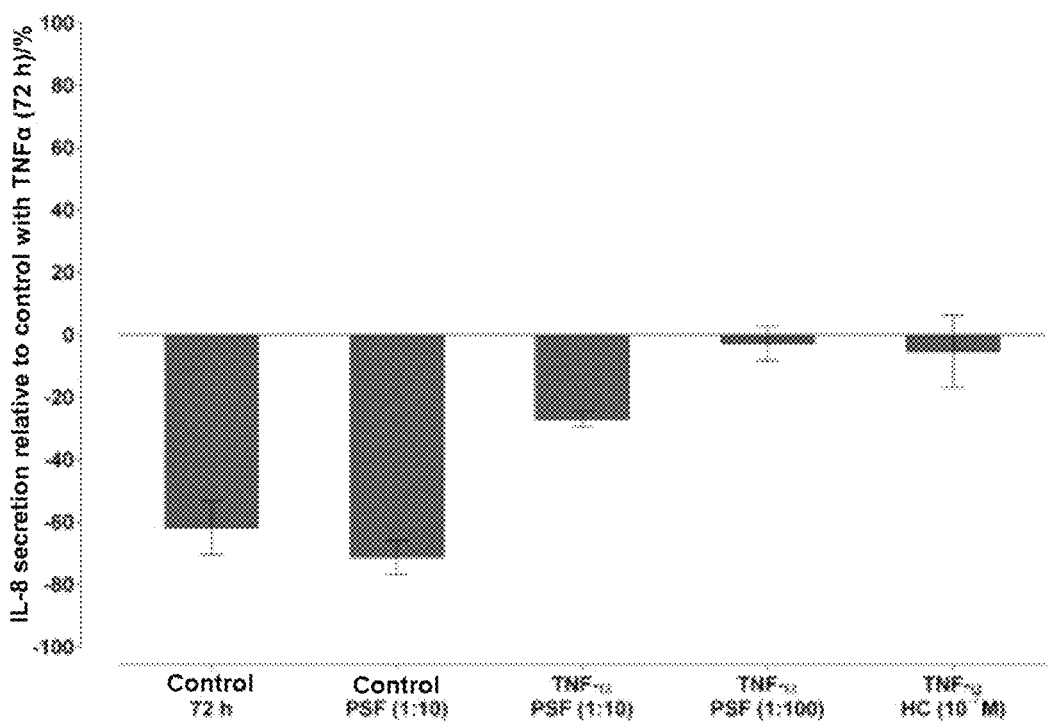
FIG. 2: IL-8 secretion relative to control with TNFα (72 h) in HaCaT cells after treatment with 10 ng/mL of TNFα (controls without TNFα) and incubation with the test substance (PSF) or hydrocortisone (HC) for 72 h (unless otherwise indicated), MV±SEM, n=3 (in triplicate respectively).

A mixture of inactivated bacteria is understood to refer to a mixture of bacteria in which the bacteria are not viable, i.e. no longer carry out metabolism and/or are incapable of proliferation. Inactivated bacteria can be obtained by radioactive or ultraviolet irradiation, heating, freezing, treatment with substances that perforate the bacterial envelope such as detergents or salts, or lysis, e.g. by exposure to a pressure drop that destroys the cell membrane (e.g. using a French press).

A lysate can be produced by lysis in which a liquid culture comprising bacteria with a desired cell count is homogenized for 10-20, 12-18, 13-17 or 14 to 16 min, for example by stirring at 50-150, 70-130 or 80-120 rpm. The homogenized liquid culture is then subjected to conventional autoclave treatment, for example heated for at least 20 min (e.g. 20-40 min, 20-30 or 20-25 min) at least 121° C. (for example, 121° C.-130° C., 121° C.-125° C. or 121° C.-123° C.), i.e. sterilized. The lysate obtained is then cooled (e.g. to 18-20° C.)

An effective amount is considered to be an amount of an ingredient sufficient to obtain a desired or therapeutic effect.

When a number is preceded by the term "approx.", this refers to a range of values of ±20%, preferably ±10%, or particularly preferably ±5% of the number in question.

The section headings serve to simplify understanding of the disclosure and do not separate one disclosure from another. In particular, each of the disclosures following a section heading can be combined with one or more other disclosures following a section heading.

Compositions

A composition is disclosed comprising an effective amount of a mixture of inactivated *Escherichia coli* and *Enterococcus faecalis*. The composition can be a pharmaceutical or a cosmetic composition.

Preferably, *Escherichia coli* is *E. coli* DSM 17252.

Preferably, *Enterococcus faecalis* is *Enterococcus faecalis* DSM 16440.

Preferably, the mixture is a mixture of *E. coli* DSM 17252 and *Enterococcus faecalis* DSM 16440.

The composition can be in the form of a lysate. Preferably, the lysate comprises all soluble and insoluble components of the bacteria and is therefore in the form of an aqueous suspension. The lysate can be obtained, for example, as described above.

The mixture of *Escherichia coli* and *Enterococcus faecalis* can be present in an amount of 1-95 wt %, 10-90 wt %, 20-80 wt %, 30-70 wt %, 40-60 wt %, 45-55 wt %, 50-54 wt % or 52-53 wt % of the total composition.

*Escherichia coli* and *Enterococcus faecalis* can be present in the mixture in a ratio of between 0.5:1.5 and 1.5:0.5, 0.75:1.25 and 1.25:0.75, or 1.15:0.85 and 0.85:1.15 or 1.05:0.95 and 0.95:1.05.

*Escherichia coli* and *Enterococcus faecalis* can be present in respective cell counts of $0.5 \times 10^7$ to $10 \times 10^7$, $1.0 \times 10^7$ to $7 \times 10^7$ or $1.5 \times 10^7$ to $4.5 \times 10^7$ per 100 g of the total mass. The term cell count refers in the case of a cell-free lysate to the number of cells used to produce the lysate.

The pharmaceutical or cosmetic composition comprises pharmaceutically acceptable excipients and/or carriers.

The composition can therefore optionally comprise the following (names according to "International Nomenclature of Cosmetic Ingredients", INCI, wherein conventional German product names are also indicated if commonly used):

*Simmondsia chinensis* seed oil, in particular 0.5 to 10 wt % or approx. 3.00 wt % of *Simmondsia chinensis* seed oil (native jojoba wax), caprylic/capric triglycerides, in particular 1-20 wt % or approx. 16.80 wt % of caprylic/capric triglycerides (medium-chain triglycerides), cera alba, in particular 0.1 to 3.0 wt % or approx. 0.50 wt % of cera alba (beeswax), hydrogenated castor oil, in particular 0.1 to 3.0 wt % or approx. 0.80 wt % of hydrogenated castor oil, cetyl PEG/PPG-10/1 dimethicone, in particular 1.0 to 4.0 wt % or approx. 2.0 wt % of cetyl PEG/PPG-10/1 dimethicone (Abil EM 180), cetyl palmitate, in particular 0.1 to 3.0 wt % or approx. 0.3 wt % of cetyl palmitate, a mixture of glyceryl dibehenate, tribehenin, glyceryl behenate, squalane, Ceramide 3, Ceramide 3B, Ceramide 6, cholesterol, in particular 0.1 to 10.0 wt % or approx. 0.5 wt % of a mixture of glyceryl dibehenate, tribehenin, glyceryl behenate, squalane, Ceramide 3, Ceramide 3B, Ceramide 6, cholesterol, phytosphingosine (wherein this mixture comprises approx. 56.0-75.0 wt % of squalane, approx. 5.0-15.0 wt % of a mixture of glyceryl dibehenate, tribehenin, and glyceryl behenate in a ratio by weight of approx. 1:1:1, approx. 1.0-5.0 wt % of a mixture of Ceramide 3 and Ceramide 3B in a ratio by weight of approx. 1:1, approx. 0.1-1.0 wt % of Ceramide 6 and approx. 5.0-15.0 wt % of a mixture of cholesterol and phytosphingosine in a ratio by weight of approx. 1:1, wherein all contents add up to 100 wt %),

*Oenothera biennis* oil, in particular 0.5 to 10 wt % or approx. 2.00 wt % of *Oenothera biennis* oil (comprising optional tocopherol in an amount sufficient to prevent oxidation, evening primrose oil stabilized with vitamin E), squalane, in particular 1.0 to 20 wt % or approx. 6.0 wt % of squalane (this amount of squalane is contained in addition to other amounts of squalane contained in the composition),

*Prunus amygdalus dulcis* oil, in particular 0.5 to 20 wt % or approx. 2.50 wt % of *Prunus amygdalus dulcis* oil (almond oil),

*Persea gratissima* oil, in particular 0.5 to 10 wt % or approx. 2.00 wt % of *Persea gratissima* oil (refined avocado oil), tocopherol acetate, in particular 0.1 to 5 wt % or approx. 0.5 wt % of tocopherol acetate (vitamin E acetate),

*Butyrospermum parkii* butter, in particular 0.1 to 5 wt % or approx. 0.5 wt % of *Butyrospermum parkii* butter (shea butter), pentylene glycol, in particular 1.0 to 5.0 wt % or approx. 4.0 wt % of pentylene glycol, glycerol, in particular 1.0 to 5.0 wt % or approx. 4.0 wt % of glycerol (glycerol 99%), sodium hyaluronate, in particular 0.01 to 0.5 wt % or approx. 0.10 wt % of sodium hyaluronate (Na hyaluronate), panthenol, in particular 0.1 to 5.0 wt % or approx. 1.0 wt % of panthenol (75% dexpanthenol), betaine, 0.1 to 5.0 wt % or approx. 0.3 wt % of betaine, magnesium sulphate, in particular 0.1 to 3.0 wt % or approx. 0.8 wt % of magnesium sulphate (magnesium sulphate heptahydrate), sodium lactate, in particular 0.05 to 1.00 wt % or approx. 0.10 wt % of 50% sodium lactate (Na lactate 50%), sodium gluconate, in particular 0.05 to 3.00 wt % or approx. 0.10 wt % of sodium gluconate, and/or lactic acid, in particular 0.01 to 1.00 wt % of lactic acid (90%) (lactic acid 90%).

Preferably, the composition comprises all of the above-mentioned excipients. All combinations of 1, 2, 3, 4, 5, 6, 7, 8, 9, 10, 11, 12, 13, 14, 15, 16, 17, 18, 19, 20, 21 and 22 of the above-mentioned excipients are also disclosed.

Preferably, the composition comprises less than 10, 9, 8, 7, 6, 5, 4, 3, 2, 1, 0.1, 0.001 or 0.0001 wt % of unsaturated fatty acids or 0 wt % of unsaturated fatty acids in free and/or esterified form. Unsaturated fatty acids are fatty acids containing at least one double bond, wherein Ceramide in this disclosure is not included among the unsaturated fatty acids and therefore can be contained in the composition.

The pH of the composition is between 4 and 6 or 4.5 and 5. The pH is preferably adjusted by adding a pharmaceutically acceptable acid, preferably an organic acid. Particularly preferably, the acid used to adjust the pH is lactic acid.

Dermatologic Conditions and Diseases

The pharmaceutical composition is used in the treatment, supportive treatment or prevention of dermatologic conditions and diseases. Preferably, the dermatologic disease and the dermatologic condition are selected from dry skin, transepidermal water loss, inflammatory skin diseases, and neurodermatitis.

In particular, the pharmaceutical or cosmetic composition is suitable for the treatment of skin diseases or skin conditions characterized by a (possibly elevated) release of interleukin 8. An elevated release of interleukin 8 is a release of interleukin 8 that is at least 5%, 10%, 20%, 30%, 40%, 50% or 100% above the secretion of interleukin 8 in a subject with healthy skin. The composition according to the invention can decrease the release of interleukin 8 by at least 10%, 20%, 30%, 40%, 50% or 100%. Interleukin 8 is released in inflamed tissue and is therefore released in the above-mentioned dermatologic diseases and dermatologic conditions. A decrease in the release of interleukin 8 is therefore characteristic of a decrease in inflammation in the affected tissue.

The dermatologic condition and dermatologic disease of "dry skin" can be characterized by excessively low fat and/or moisture content and manifests as a dull, pale appearance, low elasticity, a feeling of tension, and itching.

Transepidermal water loss (TEWL) refers to the evaporation of water from the skin not including the water loss through perspiration, as water can be released via the skin in two ways, by perspiration and by passive diffusion. The process of passive diffusion through the skin is referred to as transepidermal water loss. TEWL is strongly dependent on the integrity of the stratum corneum. TEWL is therefore a value that can be used to evaluate the condition of the skin. The composition according to the invention is suitable for reducing TEWL, in particular for reducing TEWL by at least 5%, 10%, 15%, 20%, 25%, 30%, 40% or 50%.

Any method known for this purpose can be used to determine TEWL, e.g. using unventilated chambers, ventilated champers, the vapour pressure gradient (e.g. using a Tewameter) or a Corneometer.

In the principle of measurement using a Corneometer, capacitance measurement is carried out in order to determine the skin hydration of the "outer layer" of the epidermis (stratum corneum). This principle is based on the different dielectric constants of water and other substances. A correspondingly configured measurement capacitor reacts to samples placed in its measurement volume with varying changes in capacitance, which are fully automatically detected and evaluated by the device. The active probe, which is coated with special glass, is pressed against the skin site to be measured, and after 1 second, the display shows the Corneometer measurement value, i.e. the degree of hydration of the skin surface. A special design ensures that the active end face of the probe is pressed in each case against the skin sites with constant force, including all inaccessible skin sites.

The Corneometer is composed of a pole housing and the accompanying measurement sensor. This sensor is connected to the pole housing via a helical cable with special connectors. The measurement value is displayed as a number having a maximum of three digits on the display field in the pole housing. The display field also performs additional information functions.

The measurement sensor is square-shaped. Its active end face, which is coated with special glass, is axially moveable and has a displacement of at least 3 mm. The measurement principle requires that the end face lie flat under constant pressure. In order to ensure this as reproducibly as possible, the end face of the measuring head is configured to be extremely small (7×7 mm). The inner moveable part—the active end face—is pressed against the skin by a spring with a force of 3.5 N in each case.

The Corneometer can be fully automatic. In order to carry out a measurement, the measuring head is pressed against the site on the skin to be measured. After one second, the measurement value is displayed.

The display value of the Corneometer indicates the degree of hydration of the skin surface, e.g. before and after treatment of the skin with cosmetic or pharmaceutical products, i.e. the device shows the status of or change in hydration of the skin surface.

The measurements can be carried out within a constant time window after application of the composition.

Inflammatory skin diseases are skin diseases caused by allergens, urticaria, mastocytosis, eczema, dermatitis, drug eruption, lichen, erythema nodosum, juvenile xanthogranuloma, granuloma annulare, pyoderma gangraenosum, and/or necrobiosis lipoidica. In particular, the eczemas include atopic eczema, also referred to as neurodermatitis, atopic dermatitis and endogenous eczemas.

Form of Application

The composition can be in the form of an ointment, liquid, emulsion or solution.

The composition can be topically applied in particular by external application of the composition to the skin, wherein the skin does not include the mucosa, in particular the nasal mucosa.

Application can be carried out over a period of 1, 2, 3, 4, 5 or 7 days. Application can be carried out over a period of 1, 2, 3, 4, 5 or 7 weeks, and preferably over a period of 4 weeks. Application can be carried out 1, 2, 3, 4 or 5 times per day, and preferably 2 times per day. In the case of multiple applications per day, the applications are preferably carried out at approximately equal intervals.

Particularly preferably, application of the composition is carried out over a period of 4 weeks, with application twice daily (preferably at 12 h intervals).

Production Method

Further disclosed is a method for producing a pharmaceutical composition or cosmetic composition, wherein an effective amount of inactivated *Escherichia coli* and *Enterococcus faecalis* is mixed with pharmaceutically or cosmetically acceptable excipients and/or carriers in order to obtain the above-mentioned dermatologically effective pharmaceutical or cosmetic composition.

Preferably, the composition obtained is an emulsion.

The emulsion can be produced by known methods. For example, the emulsion can be produced by the following method, wherein the amounts used correspond to the above-indicated amounts for the mixture comprising inactivated *Escherichia coli* and *Enterococcus faecalis* and for the excipients:

sodium hyaluronate is dispersed in pentylene glycol and glycerol, thus yielding a phase C;

the mixture comprising inactivated *Escherichia coli* and *Enterococcus faecalis* is blended as an aqueous solution with panthenol, betaine, magnesium sulphate, sodium lactate, sodium gluconate, and lactic acid, yielding a phase D; phase D is then added to phase C, yielding a phase E;

phase E is stirred until the sodium hyaluronate is (clearly) dissolved;

phase E is adjusted with an organic acid, e.g. lactic acid, to a pH of 4.0 to 5.5 or 4.5 to 5.0;

phase E is heated to approx. 75° C.;

a phase A is produced by mixing the components *Simmondsia chinensis* seed oil, caprylic/capric triglyceride, cera alba, hydrogenated castor oil, cetyl PEG/PPG-10/1 dimethicone, cetyl palmitate, glyceryl dibehenate, tribehenin, glyceryl behenate, squalane, Ceramide 3, Ceramide 3B, Ceramide 6, cholesterol, and phytosphingosine; phase A is heated to approx. 75° C.;

phase B is produced by mixing the components *Oenothera biennis* oil, squalane, *Prunus amygdalus dulcis* oil, *Persea gratissima* oil, tocopherol acetate, and *Butyrospermum parkii* butter; phase B is heated to approx. 50° C.;

Heated phase E is added to phase A and mixed to produce a phase AE; heated phase B is added to AE and homogenized, thus yielding a water-in-oil emulsion;

the emulsion obtained is cooled under stirring to approx. 30° C. (maximum of 30° C.) and maintained at this temperature;

The emulsion is homogenized at approx. 30° C. (maximum of 30° C.) for approx. 5 min, thus yielding the composition according to the invention as an emulsion.

The mixing steps can be carried out in a stirrer at approx. 75 rpm. The homogenization steps are carried out in a homogenizer at approx. 19,000 rpm.

Cosmetic Method

Further disclosed is a cosmetic method for increasing the elasticity and/or hydration of the skin with the composition according to the invention described above. This method is suitable in persons whose skin does not have any pathological changes whatsoever.

In the cosmetic method, the composition according to the invention can be topically applied, in particular by external application of the composition to the skin, wherein the skin does not include the mucosa, in particular the nasal mucosa.

Application can be carried out over a period of 1, 2, 3, 4, 5 or 7 days. Application can be carried out over a period of 1, 2, 3, 4, 5 or 7 weeks, and preferably over a period of 4 weeks. Application can be carried out 1, 2, 3, 4 or 5 times per day, and preferably 2 times per day. In the case of multiple applications per day, the applications are preferably carried out at approximately equal intervals.

Particularly preferably, application of the composition is carried out over a period of 4 weeks, with application twice daily (preferably at 12 h intervals).

EXAMPLES

Example 1: Effect of a Mixture Comprising Inactivated *Escherichia coli* and *Enterococcus faecalis* on the Secretion of Interleukins in HaCaT Cells In order to demonstrate the use of the composition according to the invention for the treatment of inflammatory skin diseases, tests were conducted on the reduction of cytokine secretion.

As an example, the secretion of interleukin 6 (IL-6) and interleukin 8 (IL-8) were determined. By stimulation with TNFα (10 ng/mL), interleukins can be formed in various cell types. Interleukin production can be influenced by application of anti-inflammatory agents or immunomodulators. Immunomodulating properties are tested on HaCaT cells (human adult low-calcium high-temperature keratinocytes). The cell line HaCaT (spontaneously immortalized) obtained from human, non-malignant keratinocytes (=normal skin) is derived from the healthy skin of a male patient and essentially has the properties of basal epidermal keratinocytes.

The anti-inflammatory (antiphlogistic) or immunomodulating property of a substance can be investigated e.g. in vitro on cell lines. In this test design, inflammation (upregulation of interleukin production) is induced in the cell line by external stimuli.

Test substance 1 had the following composition:

Natural enterobacteria *Enterococcus faecalis* and *Escherichia coli* in inactivated form. 1 ml of suspension contains: bacterial lysate produced from $1.5$-$4.5 \times 10^7$ cells of *Escherichia coli* (DSM 17252) and $1.5$-$4.5 \times 10^7$ cells of *Enterococcus faecalis* (DSM 16440).

Test substance 1 is applied in two dilutions to the stimulated cells, and the downregulation or modulation of interleukin production (IL-6 and IL-8) is investigated. Evaluation is carried out by ELISA (enzyme-linked immunosorbent assay). The anti-inflammatory agent hydrocortisone is also tested as a comparison substance. HaCaT cells are seeded onto a 24-well tissue culture plate with a cell density of 20,000 cells per well; after 24 h, the HaCaT cells are stimulated with TNF-α (10 ng/mL) (induction of interleukin production, e.g. IL-8), and the substances to be tested are added. After 72 h incubation, the two inflammation markers (IL-8 and IL-6) are quantitatively evaluated by ELISA.

In order to detect anti-inflammatory activity, three independent tests are carried out in triplicate.

Stimulation of the HaCaT cells with TNFα increased the secretion of interleukin 8 by a factor of 2.5 compared to the control after 72 h (FIGS. 1+2). The IL-8 secretion of the HaCaT cells incubated only with the test substance (1:10, control without TNFα) was an average of about 10% lower compared to the control at 72 h. In simultaneous addition of TNFα and the test substance (1:10), IL-8 secretion was reduced by about 27% (1:10) compared to the control with TNFα after 72 h.

In use of the test substance (1:100), it was not possible on average to detect any modification in IL-8 secretion compared to the control with TNFα after 72 h.

Figure 3:
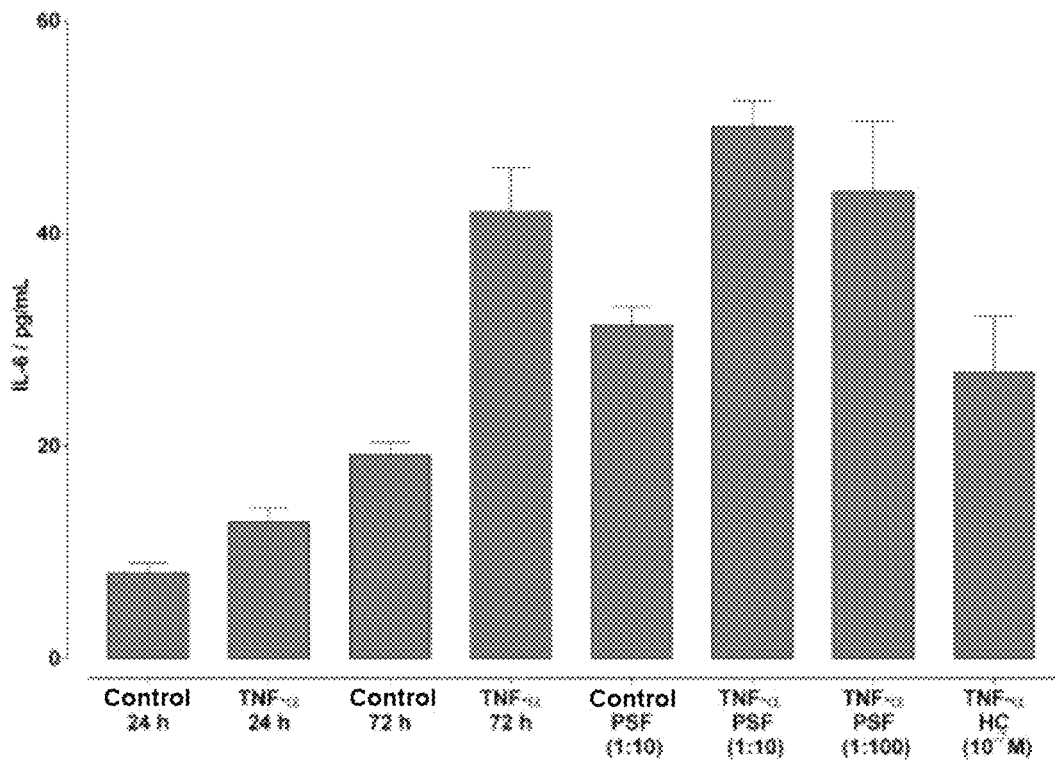
FIG. 3: Determination of IL-6 secretion in HaCaT cells after treatment with 10 ng/mL of TNFα (controls without TNFα) and incubation with the test substance (PSF) or hydrocortisone (HC) for 72 h (unless otherwise indicated), MV±SEM, n=3 (in triplicate respectively).
Figure 4:
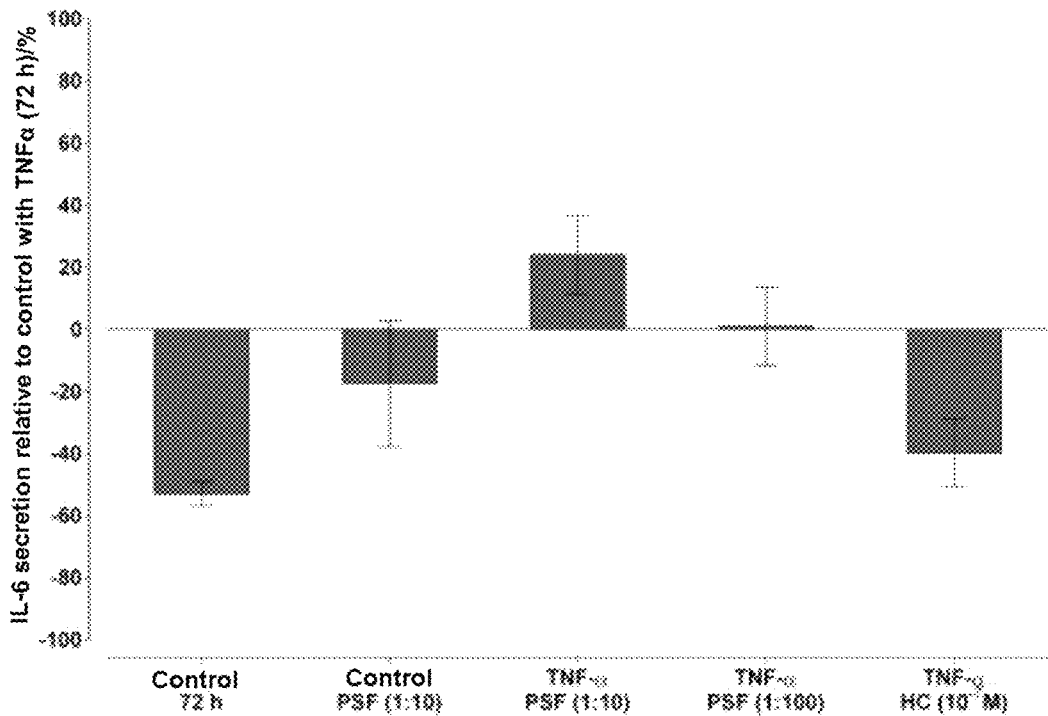
FIG. 4: IL-6 secretion relative to control with TNFα (72 h) in HaCaT cells after treatment with 10 ng/mL of TNFα (controls without TNFα) and incubation with PSF or hydrocortisone (HC) for 72 h (unless otherwise indicated), MV±SEM, n=3 (in triplicate respectively).

Secretion of interleukin 6 after stimulation with TNFα was significantly lower compared to interleukin 8 in HaCaT cells (FIGS. 3+4). After 24 h without addition of TNFα (control), IL-6 secretion was below the detection limit. In simultaneous addition of TNFα and the substance (1:10), slightly increased IL-6 secretion by an average of 24% was seen compared to the control with TNFα after 72 h.

IL-6 secretion in the 1:100 dilution of the test substance was comparable with the treated control after 72 h. In contrast to IL-8 secretion, hydrocortisone ($10^{-7}$ M) induced a significant reduction (40%) in IL-6 secretion compared to the treated control after 72 h.

The tests of the effect of the test substance on the inflammation process showed concentration-dependent modulation of release for both IL-8 and IL-6. With a 1:10 dilution of the test substance, IL-8 secretion was reduced by 27%, but IL-6 secretion was increased by 24% compared to the control with TNFα after 72 h. With a 1:100 dilution of the test substance, both IL-8 secretion and IL-6 secretion were within the range of the control with TNFα after 72 h.

Inflammation can be triggered by addition of TNFα. TNFα is a multifunctional cytokine that in addition to inflammation also modulates immune response and apoptosis. TNFα activates the immune response by initiating the occurrence of further cell divisions, considered to be inflammation markers. IL-6 is formed in the body (in vivo) after stimulation by TNFα and influences various inflammatory reactions. For example, IL-6 stimulates the formation of C reactive protein, which is often used as an acute inflammation parameter. IL-8 is a chemotactic cytokine that is expressed by various tissue and blood cells. As an inflammation mediator, IL-8 mobilizes and activates neutrophilic granulocytes and supports their degranulation. The interplay among T lymphocytes, neutrophilic granulocytes and epidermal cells presumably plays a decisive role in the pathophysiology of inflammatory skin diseases such as psoriasis.

The tests conducted on HaCaT cells after stimulation with TNFα showed that test substance 1 has a concentration-dependent effect on interleukin secretion in vitro.

Example 2: Effect of a Mixture Comprising Inactivated *Escherichia coli* and *Enterococcus faecalis* on Transepidermal Water Loss (TEWL) of the Human Skin Transepidermal water loss of the skin is one of the most important parameters for assessing the protective function of the skin. This process involves the evaporation of water from the inside of the body without including the water lost through perspiration. A preparation that maintains or improves the skin barrier function causes reduction of transepidermal water loss. Lower water evaporation from the skin corresponds to a favourable action of maintaining hydration of the skin.

Quantitative determination of transepidermal water loss (TEWL) of the skin was carried out using an evaporimeter. The measuring probe of the evaporimeter is composed of a tube open at the top with two temperature and moisture sensors attached one atop the other with a small distance between them. The two moisture sensors determine vapour pressure gradients directly in the diffusion zone above the skin. With computer support, water release in g/hm² is measured according to the Fick's law of diffusion:

$$\frac{dm}{dt} = -D \cdot A \cdot \frac{dc}{dx}$$

where
dm/dt=diffusion flow
D=diffusion coefficient
A=area
dc/dx=density gradient.

The tests of transepidermal water loss of the skin were carried out using the Tewameter® (Courage+Khazaka Electronic GmbH).

The measuring probe is placed without exerting pressure on the skin area to be tested so that the edges of the Teflon tube are flush with the skin. In total, 20 measurement cycles of a measurement series, which are recorded and averaged by the device, are carried out per test field. The test areas were located on the face, with measurement fields in a size of approx. 3 cm in diameter. Measurements were conducted at 3 different sites in these areas, and the measurement values were averaged. The measurement values obtained are shown in the tables.

The test subject collective was composed of 20 test subjects between the ages of 23 and 66. The test subjects were instructed to use test substance 2 regularly in the morning and evening for a period of four weeks.

The subjects showed extremely dry skin or skin tending toward neurodermatitis (not requiring medical treatment) in the test area.

Test substance 2 had the following composition:
3.00 wt % of *Simmondsia chinensis* seed oil,
16.80 wt % of caprylic/capric triglyceride,
0.50 wt % of cera alba,
0.80 wt % of hydrogenated castor oil,
cetyl PEG/PPG-10/1 dimethicone,
0.3 wt % of cetyl palmitate,
0.5 wt % of a mixture of glyceryl dibehenate, tribehenin, glyceryl behenate, squalane, Ceramide 3, Ceramide 3B, Ceramide 6, cholesterol and phytosphingosine (wherein the respective ingredients are present in equal portions respectively),
2.00 wt % of *Oenothera biennis* oil (stabilized with tocopherol),
6.0 wt % of squalane,
2.50 wt % of *Prunus amygdalus dulcis* oil,
2.00 wt % of *Persea gratissima* oil,
0.5 wt % of tocopherol acetate,
0.5 wt % of *Butyrospermum parkii* butter,
4.0 wt % of pentylene glycol,
4.0 wt % of glycerol (99%),
0.10 wt % of sodium hyaluronate,
52.19 wt % of test substance 1 (see example 1)
1.0 wt % of panthenol,
0.3 wt % of betaine,
0.8 wt % of magnesium sulphate,
0.10 wt % of sodium lactate,
0.10 wt % of sodium gluconate, or
lactic acid to adjust the pH to a range of 4.5 to 5.

The following tables give mean values (in g/hm²) for the TEWL measurements in the test area before and after 4 weeks of regular application respectively.

Negative values were obtained when the transepidermal water loss of the skin had decreased from the first measurement to the second measurement.

TABLE 1

Measurement results (TEWL values) in the 20 test subjects before and after 4 weeks of application of the preparation and calculation of differences before/after. Right half of the body.

|  | Before | After 4 weeks | Difference | Percentage change |
|---|---|---|---|---|
| Mean | 17.6 | 12.9 | −4.7 | −26.70 |
| Standard deviation | 27.7 | 22.1 | 4.9 | 30.25 |
| Variance | 4.8 | 4.5 | 4.0 | 24.21 |

The average change in TEWL value (%) due to application of the preparation is averaged over the individual results for the 20 test subjects. The difference in the average determined TEWL values is −4.7. This value gives the average decrease in water release after application of the preparation. With an average TEWL starting value of 17.6, this corresponds to a decrease in the transepidermal water loss of the skin of approx. −26.70%.

TABLE 2

Measurement results (TEWL values) in the 20 test subjects before and after 4 weeks of application of the preparation and calculation of differences before/after. Left half of the body.

|  | Before | After 4 weeks | Difference | Percentage change |
|---|---|---|---|---|
| Mean | 16.9 | 13.9 | −3.0 | −17.75 |
| Standard deviation | 23.0 | 23.7 | 6.2 | 106.90 |
| Variance | 3.8 | 4.4 | 3.5 | 33.25 |

The average change in TEWL value (%) due to application of the preparation is averaged over the individual results for the 20 test subjects. The difference in the average determined TEWL values is −3.0. This value gives the average decrease in water release after application of the preparation. With an average TEWL starting value of 16.9, this corresponds to a decrease in the transepidermal water loss of the skin of approx. −17.75%.

TABLE 3

Measurement results (TEWL values) in the 20 test
subjects before and after 4 weeks of application in the
control area (i.e. without application of test substance 2)
and calculation of differences before/after.

|  | Before | After 4 weeks | Difference | Percentage change |
|---|---|---|---|---|
| Mean | 10.3 | 9.8 | −0.5 | −4.85 |
| Standard deviation | 5.2 | 3.7 | 2.1 | 13.82 |
| Variance | 27.0 | 13.4 | 4.2 | 190.92 |

The average change in TEWL value (%) in the untreated control area is averaged over the individual results for the 20 test subjects. The difference in the average determined TEWL values is −0.5. This value gives the average decrease in water release without application of the preparation. With an average TEWL starting value of 10.3, this corresponds to a decrease in the transepidermal water loss of the skin of approx. −4.85%.

TABLE 4

Summary of the average changes during the observation period:

| Change in TEWL value in test field in % (right half of the body) | Change in TEWL value in test field in % (left half of the body) | Change in TEWL value in control field in % |
|---|---|---|
| −26.70 | −17.75 | −4.85 |

In this manner, it can be established that test substance 2 causes a substantial reduction in transepidermal water losses in persons with pronounced dry skin.

Example 3: Action of a Mixture Comprising Inactivated *Escherichia coli* and *Enterococcus faecalis* on Skin Hydration In the principle of measurement using a Corneometer, capacitance measurement is carried out in order to determine the skin hydration of the "outer layer" of the epidermis (stratum corneum). This principle is based on the different dielectric constants of water and other substances. A correspondingly configured measurement capacitor reacts to samples placed in its measurement volume with varying changes in capacitance, which are fully automatically detected and evaluated by the device. The active probe, which is coated with special glass, is pressed against the skin site to be measured, and after 1 second, the display shows the Corneometer measurement value, i.e. the degree of hydration of the skin surface. A special design ensures that the active end face of the probe is pressed in each case against the skin sites with constant force, including all inaccessible skin sites.

The Corneometer is composed of a pole housing and the accompanying measurement sensor. This sensor is connected to the pole housing via a helical cable with special connectors. The measurement value is displayed as a number having a maximum of three digits on the display field in the pole housing. The display field also performs additional information functions.

The measurement sensor is square-shaped. Its active end face, which is coated with special glass, is axially moveable and has a displacement of at least 3 mm. The measurement principle requires that the end face lie flat under constant pressure. In order to ensure this as reproducibly as possible, the end face of the measuring head is configured to be extremely small (7×7 mm). The inner moveable part—the active end face—is pressed against the skin by a spring with a force of 3.5 N in each case.

The Corneometer can be fully automatic. In order to carry out a measurement, the measuring head is pressed against the site on the skin to be measured. After one second, the measurement value is displayed.

The display value of the Corneometer indicates the degree of hydration of the skin surface, e.g. before and after treatment of the skin with cosmetic or pharmaceutical products, i.e. the device shows the status of or change in hydration of the skin surface.

The measurements are carried out within a constant time window after use of the product.

The test subjects were instructed to use only the test product in the specified test period for the duration of testing.

The measurements were carried out as follows:

1. The test subjects are acclimated for 45 min at a temperature of 22° C. and 60% relative hydration.

2. Skin measurement values are determined in the respective test field at three different sites. The values obtained are averaged.

3. In this test, an untreated skin area is used as a control measurement area.

4. Measurements are carried out before the beginning of use and after 4 weeks of application of test composition 2 of example 2. The respective measurements are carried out 10-12 h after the last application of the previously used product or the test products.

The respective skin hydration values per test field and time point are determined. The respective values are shown in the following tables.

The test subjects, who are specified by a serial number, their age, and their gender, are averaged, and the standard deviation is determined.

(Literature: L. Sachs, "Statistische Methoden" [Statistical Methods], 6th edition, Springer Verlag Berlin Heidelberg 1988).

delta=differences in skin hydration values delta (%)=average percentage change in hydration due to use, based on the starting value The corresponding tables show the respective values determined.

In the test area, the subjects show very dry skin or skin tending toward neurodermatitis (not requiring medical treatment).

TABLE 5

Skin hydration measurement in the treated area, right half of the body.

|  | Before | After 4 weeks | Difference | Percentage change |
|---|---|---|---|---|
| Mean | 18.3 | 27.7 | 9.4 | 51.37 |
| Standard deviation | 4.0 | 7.8 | 6.4 | 40.12 |
| Variance | 15.7 | 60.8 | 41.4 | 1609.75 |

TABLE 6

Skin hydration measurement in the treated area, left half of the body.

|  | Before | After 4 weeks | Difference | Percentage change |
|---|---|---|---|---|
| Mean | 17.7 | 27.2 | 9.5 | 53.67 |
| Standard deviation | 4.1 | 6.3 | 5.6 | 35.40 |
| Variance | 16.7 | 40.1 | 31.7 | 1252.89 |

TABLE 7

Skin hydration measurement in the untreated control area.

|  | Before | After 4 weeks | Difference | Percentage change |
|---|---|---|---|---|
| Mean | 30.6 | 32.2 | 1.6 | 5.23 |
| Standard deviation | 5.0 | 4.6 | 2.4 | 8.85 |
| Variance | 25.4 | 21.5 | 5.9 | 78.29 |

TABLE 8

Summarized evaluation of skin hydration measurements

| Change in hydration in the test field in % (right half of the body) | Change in hydration in the test field in % (left half of the body) | Change in hydration in control field in % |
|---|---|---|
| 51.37 | 53.67 | 5.23 |

In the 4-week application test, a total of 20 test subjects tolerated test substance 2 without problems according to dermatologic/clinical criteria. There were no cases of undesired or even pathologic skin changes in the test areas.

Corneometry measurement in order to test the action of test substance 2 on skin hydration was carried out in 20 test subjects using the Corneometer probe CM 825 (manufactured by Courage+Khazaka).

The change in skin hydration values was determined in the test area before and after 4 weeks of regular application of the preparations and in an untreated control area. The treated areas showed an improvement in skin hydration of 51.37% (right half of the body) and 53.67% (left half of the body). The average skin hydration change in the untreated skin area was 5.23%.

Test substance 2 therefore produced a clear improvement in skin hydration.

The invention claimed is:

1. A pharmaceutical composition in topically applicable form comprising an effective amount of a mixture of inactivated *Escherichia coli* and *Enterococcus faecalis* as well as pharmaceutically acceptable excipients and/or carriers for use in the treatment, supportive treatment or prevention of dermatologic conditions and diseases.

2. The pharmaceutical composition according to claim 1, wherein *Escherichia coli* and *Enterococcus faecalis* are present as a lysate.

3. The pharmaceutical composition according to claim 1, wherein the mixture of *Escherichia coli* and *Enterococcus faecalis* is present in an amount of 1-95 wt %, 20-80 wt %, 40-60 wt % or 45-55 wt % of the total composition.

4. The pharmaceutical composition according to claim 1, wherein *Escherichia coli* and *Enterococcus faecalis* are present in the mixture in a ratio of between 0.5:1.5 and 1.5:0.5, 0.75:1.25 and 1.25:0.75, or 1.15:0.85 and 0.85:1.15 or 1.05:0.95 and 0.95:1.05, optionally wherein *Escherichia coli* and *Enterococcus faecalis* are present in respective cell counts of $0.5 \times 10^7$ to $10 \times 10^7$; $1.0 \times 10^7$ to $7 \times 10^7$; or $1.5 \times 10^7$ to $4.5 \times 10^7$ per 100 g of the total mass.

5. The pharmaceutical composition according to claim 1, wherein the dermatologic disease and the dermatologic condition are selected from dry skin, transepidermal water loss, inflammatory skin diseases and neurodermatitis.

6. The pharmaceutical composition according to claim 1, wherein the composition is in the form of an ointment, liquid, emulsion or solution.

7. A cosmetic composition, comprising an effective amount of a mixture of inactivated *Escherichia coli* and *Enterococcus faecalis*.

8. The cosmetic composition according to claim 7, wherein the composition is in topically applicable form.

9. The cosmetic composition according to claim 7, wherein *Escherichia coli* and *Enterococcus faecalis* are in the form of a lysate.

10. The cosmetic composition according to claim 7, wherein the mixture of *Escherichia coli* and *Enterococcus faecalis* is present in an amount of 1-95 wt %; 20-80 wt %; 40-60 wt %; or 45-55 wt % of the total composition.

11. The cosmetic composition according to claim 7, wherein *Escherichia coli* and *Enterococcus faecalis* are present in a ratio of between 0.5:1.5 and 1.5:0.5; 0.75:1.25 and 1.25:0.75; or 1.15:0.85 and 0.85:1.15 or 1.05:0.95 and 0.95:1.05, optionally wherein *Escherichia coli* and *Enterococcus faecalis* are present in respective cell counts of $0.5 \times 10^7$ to $10 \times 10^7$; $1.0 \times 10^7$ to $7 \times 10^7$; or $1.5 \times 10^7$ to $4.5 \times 10^7$ per 100 g of the total mass.

12. The cosmetic composition according to claim 7, wherein the indication for cosmetic application is selected from dry skin and transepidermal water loss.

13. The cosmetic composition according to claim 7, wherein the composition is in the form of an ointment, liquid, emulsion, or solution.

14. A method for producing a pharmaceutical composition for use in the treatment, supportive treatment, or prevention of dermatologic conditions and diseases according to claim 1, which pharmaceutical composition is in topically applicable form, comprising mixing together an effective amount of inactivated *Escherichia coli* and *Enterococcus faecalis* and pharmaceutically acceptable excipients or carriers suitable for topical application, to obtain the dermatologically effective pharmaceutical composition.

15. A method for producing a cosmetic composition according to claim 7, comprising mixing together an effective amount of inactivated *Escherichia coli* and *Enterococcus faecalis* and cosmetically acceptable topically applicable excipients or carriers to obtain the dermatologically effective cosmetic composition.

16. A method for treating dry skin, transepidermal water loss, an inflammatory skin disease or neurodermatitis, comprising administering topically to the skin of a subject an effective amount of a pharmaceutical composition according to claim 1.

17. The pharmaceutical composition according to claim 1, wherein the composition is in the form of an emulsion.

18. The cosmetic composition according to claim 7, wherein the composition is in the form of an emulsion.

* * * * *